United States Patent
Kennedy et al.

(10) Patent No.: US 7,354,776 B2
(45) Date of Patent: Apr. 8, 2008

(54) METHOD OF PROCESSING AND TESTING POWDERED SAMPLES USING IMMUNOCHROMATOGRAPHIC STRIP TESTS

(75) Inventors: Tara Ann Kennedy, Wilmington, DE (US); Alan Bruce McQuillin, Newark, DE (US)

(73) Assignee: Strategic Diagnostics Inc., Newark, DE (US)

( * ) Notice: Subject to any disclaimer, the term of this patent is extended or adjusted under 35 U.S.C. 154(b) by 816 days.

(21) Appl. No.: 10/149,866

(22) PCT Filed: Dec. 14, 2000

(86) PCT No.: PCT/US00/33774

§ 371 (c)(1),
(2), (4) Date: Oct. 28, 2002

(87) PCT Pub. No.: WO01/44779

PCT Pub. Date: Jun. 21, 2001

(65) Prior Publication Data

US 2004/0033621 A1 Feb. 19, 2004

(51) Int. Cl.
*G01N 33/538* (2006.01)

(52) U.S. Cl. .............. 436/541; 435/7.32; 435/805; 435/970; 436/63; 436/174; 436/514; 436/536; 436/538; 436/807; 436/810

(58) Field of Classification Search .............. None
See application file for complete search history.

(56) References Cited

U.S. PATENT DOCUMENTS 4,959,307 A * 9/1990 Olson ................. 435/7.91
4,963,468 A * 10/1990 Olson ................. 435/7.91
5,358,690 A 10/1994 Guirguis
5,508,468 A 4/1996 Lundquist et al.
5,804,393 A * 9/1998 Geiser et al. ............ 435/7.2
5,821,073 A * 10/1998 Lee ..................... 435/7.92
5,874,662 A 2/1999 Rangan et al.
6,338,846 B1 * 1/2002 Kang et al. ............. 424/93.2
6,514,773 B1 * 2/2003 Klein et al. ............. 436/528

FOREIGN PATENT DOCUMENTS

WO WO 01/45122 A1 6/2001

OTHER PUBLICATIONS

Saxena, et al., "Insecticidal toxin in root exudates from *Bt* corn", Nature, Dec. 2, 1999, p. 480, vol. 402.
Saxena, et al., "Insecticidal toxin from *Bacillus thuringiensis* is released from roots of transgenic *Bt* corn in vitro and in situ", FEMS Microbiology Ecology, 2000, pp. 35-39, vol. 33.
Wraight et al., "Absense of toxicity of *Bacillus thuringiensis* pollen to black swallowtails under field conditions", Proceedings of the National Academy of Sciences, Jul. 5, 2000, pp. 7700-7703, vol. 97 No. 14.
Stave, James W. "Protein immunoassay methods for detection of biotech crops: Applications, limitations, and practical considerations"; *Journal of AOAC International*; vol. 83, No. 3, pp. 780-786.

* cited by examiner

Primary Examiner—Christopher L. Chin
(74) Attorney, Agent, or Firm—Kilpatrick Stockton LLP

(57) ABSTRACT

A method and kit for processing and testing powdered samples are provided herein. The powdered sample is combined with a fluid to produce a slurry or liquid suspension, and the slurry is contacted with an immunochromatographic test strip containing detectable reagents that are immunoreactive with an analyte to be detected in the sample. The method is particularly useful for the analysis of agricultural products or crops, such as the identification of recombinant grains.

15 Claims, 2 Drawing Sheets

| Strip Test Location | Trial Number | Kernel Weight, g | Butler Volume, mL | Control Line Visible | Test Line Visible | Time for "2" Control | Time for "2" Test | 3 Minute Rating | 10 Minute Rating | Time until Sink |
|---|---|---|---|---|---|---|---|---|---|---|
| :60 | | | | | | | | | | |
| Test Tube | 1 | 18.4 | 18.0 | 2:13 | 1:49 | 2:30 | 5:29 | 1.0 | 2.0 | 3:48 |
| | 2 | 18.4 | 18.0 | 3:34 | 2:20 | 3:50 | 5:30 | 1.0 | 2.5 | 4:32 |
| | 3 | 18.4 | 18.0 | 2:16 | 1:37 | 2:34 | 5:43 | 1.0 | 2.5 | 3:54 |
| | 4 | 18.4 | 18.0 | 3:41 | 1:46 | 4:00 | 5:45 | 1.0 | 2.5 | 5:57 |
| | 5 | 18.4 | 18.0 | 2:33 | 2:06 | 3:00 | 7:16 | 1.0 | 2.0 | 4:37 |
| | 6 | 18.4 | 18.0 | 3:12 | 2:40 | 3:40 | 6:55 | 1.0 | 2.0 | 3:26 |
| | 7 | 18.4 | 18.0 | 3:32 | 2:27 | 3:35 | 7:26 | 1.0 | 3.0 | 4:41 |
| | 8 | 18.4 | 18.0 | 5:40 | 2:30 | 6:00 | 8:42 | 1.0 | 2.0 | 8:32 |
| Average | | | | 3:20 | 2:09 | 3:38 | 6:35 | 1.0 | 2.3 | 4:55 |
| Standard Deviation | | | | 1:06 | 0:23 | 1:06 | 1:10 | | | 1:38 |
| Jar | 1 | 18.4 | 16.0 | 2:30 | 2:10 | 2:50 | 4:00 | 1.5 | 3.0 | 2:58 |
| | 2 | 18.4 | 16.0 | 2:13 | 2:10 | 2:43 | 3:45 | 1.5 | 5.0 | 2:27 |
| | 3 | 18.4 | 16.0 | 2:38 | 2:45 | 3:00 | 3:30 | 1.5 | 3.0 | 4:45 |
| | 4 | 18.4 | 16.0 | 2:17 | 2:17 | 2:40 | 4:53 | 1.5 | 5.0 | 2:00 |
| | 5 | 18.4 | 16.0 | 1:51 | 1:42 | 2:04 | 3:00 | 1.5 | 5.0 | 2:30 |
| | 6 | 18.4 | 16.0 | 1:51 | 1:46 | 2:11 | 3:00 | 2.0 | 5.0 | 2:30 |
| | 7 | 18.4 | 16.0 | 2:04 | 1:56 | 2:30 | 3:30 | 1.5 | 4.0 | 2:30 |
| | 8 | 18.4 | 16.0 | 2:04 | 2:00 | 2:30 | 3:30 | 1.0 | 4.0 | 2:30 |
| Average | | | | 2:11 | 2:06 | 2:33 | 3:38 | | 4.3 | 2:46 |
| Standard Deviation | | | | 0:17 | 0:19 | 0:18 | 0:36 | | | 0:50 |

FIGURE 1

| 1:125 Strip Test Location | Trial Number | Kernel Weight, g | Butter Volume, mL | Control Line Visible | Test Line Visible | Time for "2" Control | Time for "2" Test | 3 Minute Rating | 10 Minute Rating | Time until Sink |
|---|---|---|---|---|---|---|---|---|---|---|
| Test Tube | 1 | 39.3 | 40.0 | 5:32 | 4:56 | 7:19 | 7:19 | N/A | 2.0 | 7:00 |
| | 2 | 39.3 | 40.0 | N/A | 5:55 | N/A | N/A | N/A | 1.5 | N/A |
| | 3 | 39.3 | 40.0 | 8:00 | 10:00 | 8:21 | N/A | N/A | 1.0 | 10:00 |
| | 4 | 39.3 | 40.0 | 5:10 | 5:13 | 7:38 | N/A | N/A | 1.5 | 8:00 |
| | 5 | 39.3 | 40.0 | 10:00 | 4:45 | 10:00 | N/A | N/A | 0.5 | N/A |
| | 6 | 39.3 | 40.0 | 3:14 | 3:14 | 4:30 | 8:41 | N/A | 2.5 | 6:55 |
| | 7 | 39.3 | 40.0 | 4:13 | 4:15 | 5:00 | 7:00 | N/A | 2.5 | 4:31 |
| | 8 | 39.3 | 40.0 | 4:08 | 3:43 | 4:20 | 7:00 | N/A | 3.0 | 4:35 |
| Average | | | | 5:45 | 5:15 | 6:44 | 7:30 | 1.0 | 1.8 | 6:50 |
| Standard Deviation | | | | 2:24 | 2:05 | 2:10 | 0:48 | | | 2:05 |
| Jar | 1 | 39.3 | 31.0 | 3:20 | 3:00 | 3:25 | 4:45 | 1.0 | 4.0 | 4:00 |
| | 2 | 39.3 | 31.0 | 5:00 | 3:00 | 5:10 | 5:50 | 1.0 | 4.0 | 5:25 |
| | 3 | 39.3 | 31.0 | 4:00 | 2:36 | 4:45 | 5:20 | 1.0 | 4.0 | 4:00 |
| | 4 | 39.3 | 31.0 | 3:36 | 2:37 | 3:56 | 5:28 | 1.0 | 5.0 | 4:00 |
| | 5 | 39.3 | 31.0 | 3:33 | 3:00 | 3:40 | 5:32 | 0.5 | 3.0 | 4:00 |
| | 6 | 39.3 | 31.0 | 3:33 | 3:00 | 3:30 | 5:00 | 1.5 | 5.0 | 4:00 |
| | 7 | 39.3 | 31.0 | 3:00 | 2:46 | 3:30 | 5:20 | 1.0 | 3.5 | 4:00 |
| | 8 | 39.3 | 31.0 | 3:00 | 2:43 | 3:30 | 5:20 | 1.0 | 3.5 | 4:00 |
| Average | | | | 3:37 | 2:50 | 3:55 | 5:19 | 1.0 | 4.0 | 4:10 |
| Standard Deviation | | | | 0:38 | 0:10 | 0:39 | 0:19 | | | 0:30 |

FIGURE 1

METHOD OF PROCESSING AND TESTING POWDERED SAMPLES USING IMMUNOCHROMATOGRAPHIC STRIP TESTS

FIELD OF THE INVENTION

This relates to the field of immunology and more specifically relates to a method for the analysis of a powdered sample.

BACKGROUND OF THE INVENTION

Many situations exist in which it is important to have rapid, reliable, inexpensive tests that can be run by untrained individuals in the field, home, or other non-laboratory setting. Immunoassays have many of these characteristics. One type of immunoassay, referred to as an immunochromatographic or lateral flow strip test, has been successfully developed into 'one-step' tests and employed for on-site analysis. The over-the-counter home pregnancy test is an example of a simple, one-step immunochromatographic strip test.

Immunoassays have been used to detect substances in many different kinds of samples in many different markets, including the agriculture market. Modern biotechnology methods are being used to genetically modify plants. These genetically modified plants, and the seeds, grain and food derived from them all may contain novel or recombinant proteins. It is important to determine the presence of such proteins for regulatory, environmental, safety, and world trade issues. Very large amounts of grain and seed are harvested, transported, mixed, stored, distributed and traded throughout the world, and it is important to have tests that can detect these novel proteins in order to address these issues. It is desirable to have a rapid, simple and inexpensive method that can be used to test grain samples at many points along the distribution channel including trucks, elevators, barges, ships, etc. A strip test is ideally suited for this purpose. For example, recently, an immunochromatographic strip test (strip test or lateral flow device, LFD) that detects a specific protein in genetically modified soybeans was developed.

Strip tests are comprised of multiple porous components, membranes and filters, through which liquid sample is drawn by capillary action. Analyte in the sample reacts with the test reagents contained within the test strip as it traverses the length of the strip. To detect an analyte (such as a protein or mycotoxin) in grain or seed (e.g., corn, soybean, rice, wheat, etc.), it is necessary to grind the grain into a powder and then extract the protein from the powder with a liquid that is then separated from the solid material and assayed using the test. To achieve the highest sensitivity test possible, it is important to extract as much of the analyte from the grain as feasible. This requires that the grain be ground to a fine powder to facilitate efficient extraction. However, very fine particulate matter suspended in the liquid sample clogs the pores of the strip test components causing the strip to run slowly, erratically or not at all. Additional steps or test components employed to remove the particulates only serve to complicate the testing process and increase the cost of the test and time-to-result.

What is needed is a means for preparing and testing a finely ground powdered sample that maximizes extraction efficiency, sensitivity, speed and reliability of the strip test while minimizing the complexity and cost.

SUMMARY OF THE INVENTION

A method and kit for processing and testing powdered samples are provided herein. The powdered sample is combined with a fluid to produce a slurry or liquid suspension, and the slurry is contacted with an immunochromatographic test strip containing detectable reagents that are immunoreactive with an analyte to be detected in the sample. The method is particularly useful for the analysis of agricultural products, crops, or food fractions, such as the identification of recombinant grains.

It is therefore an object of the present invention to provide a rapid, reliable, and inexpensive method for analyzing an analyte in powdered samples using an immunoassay.

It is a further object of the present invention to provide an immunoassay method for the detection of analyte in a sample that is simple, portable and user-friendly and can be utilized successfully by non-scientific personnel in the laboratory and the field.

It is a further object of the present invention to provide an immunoassay device and method for the detection of analyte in a sample without requiring precise sample or reagent measurements.

It is a further object of the present invention to provide an immunoassay method for the detection of analyte in a powdered sample that provides results that are accurate and reproducible.

These and other objects of the present invention will become apparent after reading the following detailed description of the disclosed embodiments and the appended claims.

BRIEF DESCRIPTION OF THE DRAWINGS

FIG. 1 is a table showing chromatographic strip test results for the analysis of corn kernels using the method described herein.

DETAILED DESCRIPTION OF THE DISCLOSED EMBODIMENTS

A method for the detection of analyte in a sample using an immunochromatographic strip test is described herein. In accordance with the method, the sample is provided in powdered form or is processed from a solid or semi-solid sample such as a slice, granule, seed, grain, particle, or the like, to produce a powder. The powdered sample is then mixed with a fluid, such as an aqueous solution, to form a slurry or liquid suspension. The slurry is then contacted with an immunochromatographic strip.

The method and kit are useful for the detection of a wide variety of analytes including, but not limited to, agricultural products, biological and environmental contaminants or additives, industrial chemicals, toxins (particularly mycotoxins), and biological analytes, such as antigenic determinants of proteins, polysaccharides, glycoproteins, lipoproteins, nucleic acids and hormones, of organisms such as viruses, bacteria, fungi, parasites, plants and animals, including large and small molecules, polymers and haptens. The method is particularly useful for the identification or quantification of proteins or peptides in genetically modified plants or recombinant agricultural products, such as grains. For example, the method is useful for the detection of the *Bacillus thuringiensis* Cry1Ab or Cry1Ac proteins in genetically modified plants, such as corn, as described below in the examples.

Definitions

The terms "a", "an" and "the" as used herein are defined to mean "one or more" and include the plural unless the context is inappropriate.

The term "analyte" refers to a drug, hormone, chemical, toxin, compound, receptor, nucleic acid molecule or other molecule and fragments thereof to be measured by the method described herein.

Sample Processing Method Development

During the development of an immunochromatographic strip test to detect the *Bacillus thuringiensis* Cry1Ab protein in genetically enhanced corn kernels, great difficulty was encountered in achieving the sensitivity and time-to-result specifications that are required of the commercial product. Data demonstrated that increasing grinding time of the corn kernels increased extraction efficiency and test sensitivity. However, the more finely ground particles in the liquid sample caused the test to flow too slowly.

To increase sensitivity, less liquid was added to the ground powder to minimize the dilution of the analyte in the sample, but this resulted in even more particulate matter in the liquid sample and poorer performing tests. In fact, in some experiments, the amount of liquid added to the powdered corn was reduced to the point that there was only enough liquid to suspend the powder but no remaining liquid to pull off and test. At this point, lacking any liquid sample to test, the end of the strip test was inserted directly into the wet, powdered corn slurry. The expectation was that the thick slurry would clog the strip, but, surprisingly, the strip flowed significantly faster than when tested with liquid pulled from the sample. Further experimentation demonstrated that the sensitivity and reliability of the test were also significantly improved and addition of the strip directly to the powdered slurry eliminated the step of transferring the liquid sample to a separate vessel, thereby reducing the number of components and complexity of the test.

Sample Processing

A sample is collected or obtained using methods well known to those skilled in the art. The sample containing the analyte to be detected may be obtained from any biological or environmental source. For example, the sample may be any plant tissue or extract including root, stem, leaf, or seed. The sample may be diluted, purified, concentrated, filtered, or otherwise manipulated prior to being mixed with the fluid to create a slurry or liquid suspension to optimize the assay results.

Analytes to be detected using the immunoassay method described herein include, but are not limited to, the following analytes: molecules, such as organic and inorganic molecules, peptides, proteins, glycoproteins, carbohydrates, nucleic acids, lipids, toxins, and the like. Analytes also include but are not limited to neurotransmitters, hormones, growth factors, antineoplastic agents, cytokines, monokines, lymphokines, nutrients, enzymes, receptors, antibacterial agents, antiviral agents, and antifungal agents. The term analyte also means detectable components of structured elements such as cells, including all animal and plant cells, and microorganisms, such as fungi, viruses, bacteria including but not limited to all gram positive and gram negative bacteria, and protozoa. The term analyte also means detectable components of organelles and cells.

The sample is ground, homogenized, chopped, blended, or otherwise manipulated to create a powder. The size and texture of the powder or fine granules can be adjusted by modifying the technique or increasing the amount of manipulation time, such as grinding or blending, as needed.

The fluid with which the powdered sample is combined or mixed is one capable of forming a slurry or liquid suspension. The preferred fluid is an aqueous solution, such as a buffer that is compatible with the immunochromatographic strip.

Immunochromatographic Strip

The immunochromatographic strip, or detection membrane, is a membrane or strip having reagents deposited in zones along the longitudinal length of the membrane. Immunochromatographic strips are readily available from commercial suppliers or can be customized by laboratory personnel skilled in the art, or a commercial immunodiagnostic supplier, to include immunoreagents specific for the analyte to be detected. The immunoassay reactions conducted on the strip may be in competitive or sandwich immunoassay formats The reagents suspended or immobilized on the membrane provide means for detecting analyte, preferably by visually detecting a labeled substance or substances, such as colloidal gold, that have been bound to analyte. Alternatively, the reagents may detect the absence of labeled substance, and the label may be detected using instrumentation know to those skilled in the art such as a spectrophotometer or fluorescence detector. The reagents on the membrane may be immobilized or may be diffusible but contained on the membrane in a solid or semi-solid state that, when contacted with the sample, becomes mobile and moves with the sample toward the distal end of the membrane. Reagents may also be included on the immunochromatographic strip to enhance or clarify the signal produced by the label being detected. Additional reagents are optionally incorporated in zones on the detection membrane for calibration.

The membrane is preferably a non-woven substrate upon which the reagents can be immobilized or deposited, and which is capable of conveying sample in a fluid flow direction generally parallel to the longitudinal length of the chromatographic strip. Desirable chromatographic strips are composed of a fluid-conducting material including, but not limited to, nylon, polyethylene, glass fiber, nitrocellulose, cellulose, and other common membrane matrices or bibulous materials. The preferred chromatographic strip is composed of nitrocellulose. The membrane of the chromatographic strip is optionally backed with, or laminated to, another material. Desirable backing or laminating material is polyethylene or vinyl, although other suitable materials known in the art may be used.

A reagent sink is optionally included at the distal end of the immunochromatographic membrane or strip for enhancing the flow of the fluids, including reagents and sample, along the longitudinal length of the strip. The sink may be composed of an absorbent material, such as blotting paper.

Optionally included in flow communication with the distal end of the strip is an end of test indicator for indicating completion of the assay. The end of test indicator may be included in the reagent sink described above or may be a separate component located at the distal end of the immunochromatographic strip or reagent sink, if present.

The end of test indicator is preferably composed of an absorbent material containing an indicator, or dye, that travels with the liquid to indicate that the liquid has traveled to the distal end of the strip and that the strip is ready for analysis. Analysis can be conducted either by visual inspection or with the aid of instrumentation. Preferably, movement of the dye through the absorbent material to a predetermined location is visually detectable.

Kit

An immunoassay kit for the detection of analyte in a sample provided herein contains a fluid, such as a buffer to be combined with the powdered sample to form a slurry or liquid suspension, and an immunochromatographic strip or membrane. The kit may optionally contain one or more antibodies or other reagents to combine with the sample prior to contacting the sample slurry with the membrane.

The kit may additionally contain additional reagents or buffers, equipment for obtaining or collecting the sample, a vessel for containing the sample and reagents, a timing means, and a calorimeter, reflectometer, or standard against which a color change may be measured. A simple, inexpensive reflectometer is preferred.

The reagents, including any antibody reagents may be lyophilized, in a single vessel or in individual vessels. Addition of the slurry sample to the vessel results in solubilization of the lyophilized reagents, causing them to react.

The method and kit as described above will be further understood with reference to the following non-limiting examples.

EXAMPLE 1

Genetically Modified Corn Sample Preparation and Analysis

This example illustrates the use of the method described herein to detect the Cry1Ab protein in a genetically modified, insect-resistant corn sample.

Each sample was weighed to obtain the proper number of corn kernels. Samples containing 60 kernels weighed 18.4 g and samples containing 125 kernels weighed 39.3 g.

Each sample was placed in a clean and dry glass, 4 oz. MASON™ jar.

A 70 mm blender base and blade assembly (Eberbach Co., Ann Arbor, Mich.) was attached. The MASON™ jar was placed onto the laboratory grade blender (Waring Model 31BL91) and covered with a safety shield. The sample was ground on high speed for 30 seconds to produce powdered corn. The safety shield, adapter and blade were removed.

The following specified amounts of buffer (Trait$_\sqrt{}$™, also referred to as "Traitcheck", sample buffer, Strategic Diagnostics Inc., Newark, Del.) was added to the powdered corn directly in the MASON™ jar. For the test tube procedure, 60 kernel samples were combined with 18.0 mL of buffer. The 125 kernel samples required 40.0 mL of buffer to produce a slurry or liquid suspension. For samples run directly in the MASON™ jar, 60 kernel samples used 16.0 mL of buffer, and 125 kernel samples required only 31.0 mL of buffer.

The MASON™ jar lid was attached to the MASON™ jar and the contents shaken for approximately 30 seconds, until all the ground corn was evenly and thoroughly wet.

For samples run in the test tube, the MASON™ jar lid was removed, and the sample allowed to settle approximately 30 seconds. A 500 µL aliquot of extract was pipetted off and placed in a test tube. A chromatographic test strip, upon which was immobilized antibody having immunospecificity for the Cry1Ab protein of Bacillus thuringiensis, was inserted into the extract until it reached the bottom of the test tube.

For samples run directly in the MASON™ jar, the MASON™ jar lid was removed and the chromatographic strip inserted into the corn mixture. The strip was immersed until the check mark ($\sqrt{}$) on the filter cover was reached (approximately 16 mm).

Each strip was allowed to run for 10 minutes at room temperature. Various readings were taken, including time until control line was visible, time until test line was visible, times for control and test, readings at 3 minutes and 10 minutes, and time until the reagents reached the sink.

The results are shown in FIG. 1. A detailed user guide describing the products and procedures for analysis of the Cry1Ab protein in a genetically modified corn sample is provided in Example 2, below.

EXAMPLE 2

Lateral Flow Test Kit and Procedure for the Detection of Cry1Ab Protein

This example a detailed procedure and kit to detect a Cry1Ab protein in a genetically modified, insect-resistant corn sample.

Kit Description

A kit is used to detect the Cry1Ab protein produced by a gene derived from Bacillus thuringiensis. This gene has been incorporated into insect-resistant corn including YIELDGARD™ brands from both Monsanto and Novartis. The intended uses of the kits include the qualitative (yes/no) determination of the Cry1Ab protein in plant leaf and seed tissue and corn grain samples. The lateral flow strips and other components provided in the kit are sufficient to make qualitative determinations for the presence of absence of the Cry1Ab protein in both field and laboratory environments. Different application protocols are required for leaf, seed and bulk grain determinations.

Principle of the Assay

The assay uses a double antibody sandwich format. Antibodies specific to the Cry1Ab protein are coupled to a color reagent and incorporated into the lateral flow strip. When the lateral flow strip is placed in a small amount of an extract from plant tissue that contains Cry1Ab protein, binding occurs between the coupled antibody and the protein. A sandwich is formed with some, but not all the antibody that is coupled to the color reagent. The membrane contains two capture zone, one captures the bound Cry1Ab protein and the other captures unreacted antibodies coupled to the color reagent. These capture zones display a reddish color when the sandwich and/or unreacted colored reagents are captured in the specific zones on the membrane. The presence of only one line (control line) on the membrane indicates a negative sample and the presence of two lines indicates a positive sample.

Contents of Kit

100 Bacillus thuringiensis (Bt1) chromatographic Test Strips
100 or more Sample cups
100 or more Wooden spatulas
1 User guide Material Required but not Supplied Trait$_\sqrt{}$™, also referred to as "Traitcheck", sample buffer (Strategic Diagnostics Inc., Newark, Del.)
Laboratory grade blender (Waring Model 31BL91 recommended)
Waring adapter for MASON™-type jars
MASON™ 4 oz. Blender jars*
Graduated cylinder, 50 ml (60 ml)
*Caution: A shield should be used over the blender jars while grinding. Safety glasses should be used.

Preparation and Storage of Reagents

Trait√™ sample extraction buffer for grain is shipped as a concentrate. Follow the procedure below to prepare the product to be used for sample extraction:
1. Pour the contents of a one liter bottle of Trait√™ Sample Buffer Concentrate into a 5-8 liter carboy or other suitable container.
2. Add four liters of water to the sample buffer. Tap water may be used.
3. Mix well and label as Trait√™ Corn Sample Buffer. Label buffer expiration as six months from date of preparation.

The Trait√™ Corn Sample Buffer may be stored at room temperature.

Bt1 Corn Grain Test Kit: User Guide

The Lateral Flow Test Kit should be stored at room temperature. The Bt1 Test Strips must be kept in the foil pouch with desiccant. Storage conditions higher than room temperature may adversely affect performance.

Sampling

The samples used for the Bt1 Corn Grain Test Kit can be sub-samples of those "representative samples" collected from trucks, railcars, barges, etc. for other tests. The size of the sub-samples to be used for the test will depend on the level of genetically modified corn kernels at which the screening is being conducted and an acceptable level of risk that the genetically modified level is close to the screening level. The number and size of the sub-samples is discussed in more detail in the application protocol section below.

It is assumed that the samples collected are representative of the contents of the truck or container and are sufficiently mixed to contain a random distribution of the sample contents.

Sample Preparation: Weighing the Sample

The statistical sampling plan (see Principle of the Screening Application) is dependent on the number of corn kernels used. It is more practical to weigh corn kernels to obtain the correct sub-sample size, however, the number of corn kernels in a unit weight depends on the variety of corn and environmental conditions.

The table below is a guideline for the weight to corn kernel number ration for seed corn.

| Average Weight of Seeds (Iowa State University) | |
| --- | --- |
| Seed Size | Average Grams/Seed |
| Very small | 0.188 |
| Small | 0.219 |
| Medium | 0.257 |
| Large | 0.316 |

However, it is recommended that the ratio for each variety be determined as follows:
1. Count 100 corn kernels of the variety to be tested.
2. Weigh the 100 kernels to the nearest 0.01 gram
3. Divide the weight of the corn kernels by 100 to get the average grams per corn kernel (the result will be less than one gram per corn kernel).
4. Multiply this average weight by the desired number of corn kernels in the sub-sample to determine the weight for the sub-samples.
5. Construct a table for each variety for the different sub-sample sizes to be used.

Example: One hundred corn kernels of Varietyx weigh 35.00 grams. Each corn kernel then weighs 0.35 grams. Multiply the 0.35-gram per corn kernel times the number of corn kernels in each sample size to get the following table:

| Example of Weight-to-Corn kernel Ratio Table | | | | |
| --- | --- | --- | --- | --- |
| | Variety X:Grams per Sample | | | |
| Corn kernels | 40 | 60 | 70 | 125 |
| Weight (g) | 14.0 | 21.00 | 24.5 | 43.75 |

Note:
The National Corn Growers Association (web site) states that typical corn is 56 lbs. For a bushel of about 72,800 kernels or 0.350 g/kernel.

This average weight is then used to determine the weight of corn kernels that will be used to represent the number of corn kernels (for this variety) selected in the Probability Tables.

Sample Preparation: Processing the Sample

The preparation of the sample is very important for the proper function of the test, especially the ratio of extraction buffer to the weight of the corn sample. The following table contains recommendations for the amount of Trait√™ Corn Sample Buffer for extraction based on the sample weight. A 4 oz MASON™ jar and a grinding time of 15 seconds on high speed is used for all the sample sizes (40, 60, 70, and 125 kernels) used in this example. The processing parameters were determined using the laboratory grade Waring Model 31BL91 food processor. Other food processors or extreme sized corn kernels will require further validation.

| Parameters for Preparing Samples | |
| --- | --- |
| Weight Range (grams) | Buffer Volume (ml)* |
| 5-10 | 10 |
| 13-21 | 20 |
| 22-29 | 25 |
| 30-39 | 35 |
| 40-48 | 45 |

Note: the buffer volume is very important and should be measured carefully.
1. Weigh two sub-samples from each truck or container.
2. Place each sub-sample in a dry MASON™ jar.
3. Attach the jar adapter and dry cutting blades.
4. Place the jar onto the food processor, place a shield over the jar and grind the sub-samples for 15 seconds on high speed. (It is very important to shield the jars since breakage can occur.)
5. Remove the adapter and cutting blades.
6. Add Trait√™ Corn Sample Buffer, prepared as described above, t the ground corn kernels in the jar, place a lid on the jar and shake the jar until all the ground corn kernels are well wetted (about 10-20 seconds)
7. Use this sample extract for the Test Procedure.

Note: it is important to clean and dry the jars and cutting blades between samples.

Equipment Cleaning and Drying
1. The MASON™ jar should be emptied, rinsed well with water and completely dried with a paper towel between uses.
2. The cutting blades for the blender should be rinsed, wiped clean, sprayed or rinsed with methanol and dried with a paper towel between uses.

Test Procedure
1. With a wooden spatula from the kit, transfer sufficient sample to the sample cup to fill about level full and smooth the top surface of the sample.
2. Place one Bt1 Test Strip into the sample cup with the arrows pointing into the cup. The test strip should just touch or be very close to the bottom of the sample cup. Let sit until the control line (top line) is clearly visible then determine if the test line is visible. This may require 5-8 minutes.
3. The appearance of a single line (control) near the top of the strip indicates a negative result.
4. The appearance of two lines on the strip indicates a positive result.

Reading the Lateral Flow Test Strip
1. Insert the labeled filter cover of the test strip into the sample cup containing the wet corn sample. The arrows on the filter cover should point into the cup. The test trip contains a test strip top (reservoir pad where sample is contacted), a result window below the test strip top, and a test strip bottom (labeled filter cover).
2. Check the result window frequently after adding the strip. At least one line, the control line, should always develop approximately 1 cm down from the reservoir pad. The control line contains an antibody specifically immunoreactive with a common corn protein, but not a Bt protein. A red line in this position indicates that the device is functioning properly. A red line appearing below the control line is the test line, which contains monoclonal antibodies specifically immunoreactive with the Bt protein, and, if visible, indicates a positive results. If the test strip displays two red lines, the test is complete and the sample is positive for Cry1Ab Bt corn kernels. If, after approximately eight minutes, the test strip only shows a clearly visible control line, then the sample is negative for Cry1Ab Bt corn.

Principle of the Screening Method

The test strip contains immobilized immunologic (antibody) reagents that react with the recombinant Bt proteins present in genetically modified corn that has been engineered to include one or more genes for Bt proteins. As the sample migrates down the chromatographic strip, it reacts with the immobilized antibodies and generates a visible, colorimetric signal, thereby providing a yes/no answer for the presence or absence of Cry1Ab Bt corn kernels in a given sample. One red line at the top of the test strip indicates a negative result and two red lines, the second line lower on the test strip, indicates a positive result for the presence of Cry1Ab corn kernels. Testing two statistically selected sub-samples allows an estimate of the percent of Cry1Ab Bt corn kernels. Te test results can provide information about the probability of the percent in the representative sample being within certain ranges. (Note: this test protocol will not specifically determine the percent of genetically modified corn kernels.)

The statistical model used for this method is the Poisson Probability Distribution which provides good approximations to binomial (yes/no) probabilities when the number of items tested (i.e. corn kernels) is large but the probability of a positive result is expected to be small (i.e. low level of genetically modified corn kernels). Using the Poisson Probability Distribution, it is possible to determine the probability of having zero genetically modified corn kernels in a random sample of a given size (number of corn kernels) at a given percent genetically modified corn. For example, a random sub-sample of 100 corn kernels selected from a larger sample at one percent genetically modified corn has a 36.8% probability of containing no genetically modified corn kernels. The probability of a 75 corn kernel sub-sample (at one percent genetically modified) containing zero genetically modified corn kernels is 47.2%.

Alternatively, for a 100 corn kernel sub-sample of unknown percent genetically modified, a single negative test result provides the information that the representative sample has a 60.7% probability of having 0.5% or less genetically modified corn kernels, 36.8% probability of 1% or less genetically modified corn kernels and 13.5% probability of having 2% or less genetically modified corn kernels.

Using two sub-samples instead of one increases the confidence of estimating the genetically modified range. The application protocols developed for screening corn by using this test kit use two sub-samples of equal number of corn kernels. The size of the two sub-samples is determined by the desired screening level and the level of risk tolerance. If screening at 1% genetically modified level or higher, a passing results is achieved if one or both sub-samples are negative for Cry1Ab Bt corn kernels. If screening at 0.5% (or lower) the decision criterion is changed so that both sub-samples must be negative to pass the sample.

The following probability tables provide guidelines for selection of the two sub-sample sizes for screening at different genetically modified (GM) corn kernel levels.

| Probability Tables | | | | | | |
|---|---|---|---|---|---|---|
| Screening at 3.0% genetically modified (GM) corn: Pass is one or two negative results | | | | | | |
| | Probability of sample passing (%) | | | | | |
| GM % | 1.0 | 2.0 | 3.0 | 4.0 | 5.0 | 7.5 |
| 30 kernels | 83.3 | 77.6 | 64.8 | 51.2 | 39.7 | 20.0 |
| 40 kernels | 89.1 | 69.7 | 51.2 | 36.6 | 25.2 | 9.7 |
| 50 kernels | 84.5 | 60.0 | 39.7 | 25.2 | 15.7 | 4.7 |
| Screening at 2.0% genetically modified (GM) corn: Pass is one or two negative results | | | | | | |
| | Probability of sample passing (%) | | | | | |
| GM % | 0.5 | 1.0 | 2.0 | 3.0 | 4.0 | 5.0 |
| 50 kernels | 95.1 | 84.5 | 60.0 | 39.6 | 25.2 | 15.7 |
| 60 kernels | 93.3 | 79.6 | 51.2 | 30.3 | 17.3 | 9.7 |
| 75 kernels | 90.2 | 72.2 | 39.6 | 20.0 | 9.7 | 4.6 |
| Screening at 1.0% genetically modified (GM) corn: Pass is one or two negative results | | | | | | |
| | Probability of sample passing (%) | | | | | |
| GM % | 0.25 | 0.5 | 1.0 | 2.0 | 3.0 | 4.0 |
| 100 kernels | 95.1 | 84.5 | 60.0 | 25.2 | 9.7 | 3.6 |
| 125 kernels | 92.8 | 78.4 | 49.1 | 15.7 | 4.6 | 1.3 |
| Screening at 0.5% genetically modified (GM) corn: Pass is two negative results | | | | | | |
| | Probability of sample passing (%) | | | | | |
| GM % | 0.1 | 0.25 | 0.5 | 1.0 | 2.0 | 3.0 |
| 50 kernels | 90.5 | 77.9 | 60.7 | 36.8 | 13.5 | 5.0 |
| 70 kernels | 86.9 | 70.5 | 49.7 | 24.7 | 6.1 | 1.5 |
| 90 kernels | 83.5 | 63.8 | 40.7 | 16.5 | 2.7 | 0.5 |

Note: the 0.5% screening level requires both of the two sub-samples to be negative to pass the sample.

Interpretation of Test Results

Using the Probability Table for the 2% genetically modified corn kernel screening level as an example, the recommended size of the two sub-samples is 60 corn kernels. The two sub-samples of 60 corn kernels each are tested. The test can determine if either zero corn kernels (negative) or one or more genetically modified corn kernels (positive) are in each sub-sample. The test cannot determine if a positive sub-sample has only one genetically modified corn kernel or several genetically modified corn kernels. The "fail" criterion is when both sub-samples are positive.

Using two sub-samples of 60 corn kernels with the above decision criteria, samples at the following genetically modified corn kernel levels will have the indicated statistical probabilities of passing the test:

| GM Corn Kernels (%) | Probability of Pass (%) |
| --- | --- |
| 0.5 | 93.3 |
| 1.0 | 79.6 |
| 2.0 | 51.2 |
| 3.0 | 30.3 |
| 5.0 | 9.7 |

A 60-corn kernel sub-sample for a 2% screening level has the risks associated with the above statistical probabilities. If a lower risk of accepting a "more contaminated" sample is desired, then a 75-corn kernel sub-sample can be chosen for the 2% screen. With this size for the two sub-samples, the probability of passing a 5% contaminated sample, for example, is reduced to 4.6%. However, probabilities of passing "good" samples (i.e. below 2% genetically modified) are also reduced. Likewise, if more risk can be tolerated, 50-corn kernel sub-samples used with this decision criterion will pass 60% of samples at 2% and 15.7% at 5%.

Screening at Below 1% Genetically Modified Screening Level

Because of the sensitivity of the strip test described in this example, screening at levels lower than 10.% genetically modified corn requires different criteria. The decision criteria are that a sample passes if both sub-samples results are negative for genetically modified corn. The sample will fail if one or both sub-samples are positive. Using two 70-kernel sub-samples and the criteria that two negative results is a "pass", the probability of passing a trick at 0.5% is 49.7%, at 0.25% is 70.5% and at 1% is 24.7%.

The use of two sub-samples is recommended for screening at all genetically modified levels. In all cases, the recommended sub-sample size has been chosen to provide about a 50/50 probability of passing a representative sample at the screening level. However, by making changes to the sub-sample size, those probabilities can be changed.

Modifications and variations of the present method and kit will be obvious to those skilled in the art from the foregoing detailed description. Such modifications and variations are intended to come within the scope of the appended claims.

What is claimed is:

1. A method for detecting analyte in a powdered sample comprising combining the powdered sample with a buffer to form a slurry, wherein the slurry is free from excess liquid, contacting the slurry with an immunochromatographic strip, and detecting analyte on the strip, wherein the strip contains a detectable reagent immunoreactive with the analyte; and, wherein the powdered sample is an agricultural product.

2. The method of claim 1 wherein the strip is inserted directly into the slurry.

3. The method of claim 1 wherein the sample is a grain.

4. The method of claim 1 wherein the sample is corn.

5. The method of claim 1 wherein the sample is a genetically modified plant.

6. The method of claim 1 wherein the analyte is a protein.

7. The method of claim 1 wherein the analyte is a recombinant protein.

8. The method of claim 1 wherein the analyte is a recombinant *Bacillus thuringiensis* protein.

9. The method of claim 8 wherein the analyte is a Cry1Ab protein.

10. The method of claim 8 wherein the analyte is a Cry1Ac protein.

11. A method for detecting analyte in a powdered sample comprising
combining the powdered sample with a buffer to form a slurry, wherein the slurry is free from excess liquid,
contacting the slurry with an immunochromatographic strip, wherein the strip is inserted directly into the slurry, and
detecting analyte on the strip,
wherein the strip contains a detectable reagent immunoreactive with the analyte.

12. The method of claim 11 wherein the powdered sample is an agricultural product.

13. The method of claim 12 wherein the powdered sample is a grain.

14. The method of claim 12 wherein the powdered sample is a genetically modified plant.

15. The method of claim 11 wherein the analyte is a recombinant protein.

* * * * *